(12) United States Patent
Wang et al.

(10) Patent No.: US 8,337,739 B2
(45) Date of Patent: Dec. 25, 2012

(54) IMPROVING FRACTURE TOUGHNESS OF MEDICAL DEVICES WITH A STEREOCOMPLEX NUCLEATING AGENT

(75) Inventors: Yunbing Wang, Sunnyvale, CA (US); James Oberhauser, Saratoga, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 0 days.

(21) Appl. No.: 12/190,497

(22) Filed: Aug. 12, 2008

(65) Prior Publication Data
US 2010/0038822 A1    Feb. 18, 2010

(51) Int. Cl.
*B28B 21/56* (2006.01)
(52) U.S. Cl. ........ 264/294; 264/523; 264/540; 264/537; 264/539; 264/288.4; 264/290.2; 264/291
(58) Field of Classification Search .................. None
See application file for complete search history.

(56) References Cited

U.S. PATENT DOCUMENTS

| | | | |
|---|---|---|---|
| 5,211,902 A | 5/1993 | Unger et al. | |
| 6,319,576 B1 | 11/2001 | Rule et al. | |
| 6,932,930 B2 | 8/2005 | DeSimone et al. | |
| 2003/0083732 A1* | 5/2003 | Stinson | 623/1.15 |
| 2004/0181271 A1 | 9/2004 | Desimone et al. | |
| 2006/0246108 A1* | 11/2006 | Pacetti et al. | 424/426 |
| 2007/0132156 A1 | 6/2007 | Burgermeister et al. | |
| 2007/0200271 A1 | 8/2007 | Dave | |
| 2007/0253996 A1 | 11/2007 | Bin et al. | |
| 2007/0253999 A1 | 11/2007 | Huang et al. | |
| 2007/0283552 A1* | 12/2007 | Gale et al. | 29/515 |
| 2008/0014240 A1 | 1/2008 | Gale et al. | |
| 2008/0051873 A1 | 2/2008 | Cottone et al. | |
| 2008/0177374 A1 | 7/2008 | Zheng et al. | |
| 2010/0025894 A1 | 2/2010 | Kleiner et al. | |
| 2010/0036478 A1 | 2/2010 | Wang et al. | |
| 2010/0038822 A1 | 2/2010 | Wang et al. | |

FOREIGN PATENT DOCUMENTS

| | | |
|---|---|---|
| EP | 1 872 808 | 1/2008 |
| WO | WO 2007/142736 | 12/2007 |
| WO | WO 2008/008495 | 1/2008 |
| WO | WO 2010/017090 | 2/2010 |
| WO | WO 2010/019478 | 2/2010 |

OTHER PUBLICATIONS

U.S. Appl. No. 12/059,423, filed Mar. 31, 2008, Wang.
Anderson et al., "Melt preparation and nucleation efficiency of polylactide stereocomplex crystallites", Polymer, vol. 47, pp. 2030-2035 (2006).

(Continued)

*Primary Examiner* — Khanh Nguyen
*Assistant Examiner* — Margaret Squalls
(74) *Attorney, Agent, or Firm* — Squire Sanders (US) LLP

(57) ABSTRACT

Methods of fabricating a polymeric implantable device from a PLLA/PDLA blend such as a stent with improved fracture toughness are disclosed. The blend is melt processed to allow formation of stereocomplex crystallites, which are nucleation sites for crystal growth. A polymer construct is formed from the melt processed blend and device is formed from the polymer construct. The stereocomplex crystallites result in an in increase in nucleation density and reduced crystal size, which increases fracture toughness of the formed device.

23 Claims, 6 Drawing Sheets

OTHER PUBLICATIONS

Brizzolara et al., "Mechanism of the Stereocomplex Formation between Enantiomeric Poly(lactide)s", Macromolecules, vol. 29, pp. 191-197 (1996).

Kawamoto et al., "Nucleating-Agent for Poly(L-lactic acid)—An Optimization of Chemical Structure of Hydrazide Compound for Advanced Nucleation Ability", J. of Applied Polymer Science, vol. 103, pp. 198-203 (2007).

Krouse et al., "Stereocomplex Formation between Enantiomeric Poly(lactides)", Macromolecules, vol. 20, pp. 904-906 (1987).

Schmidt et al., "Polylactide Stereocomplex Crystallites as Nucleating Agents for Isotactic Polylactide", Journal of Polymer Science: Part B: Polymer Physics, vol. 39, pp. 300-313 (2001).

Takasaki et al., "Development of Stereocomplex Crystal of Polylactide in High-Speed Melt Spinning and Subsequent Drawing and Annealing Processes", Journal of Macromolecular Science: Part B—Physics, vol. B42, Nos. 3 & 4, pp. 403-420 (2003).

Tsuji et al., "Stereocomplex Formation between Enantiomeric Poly(lactic acid)s. 2. Stereocomplex Formation in Concentrated Solutions", Macromolecules, vol. 24, pp. 2719-2724 (1991).

Tsuji et al., "In vitro hydrolysis of blends from enantiomeric poly(lactide)s. Part 4: well-homo-crystallized blend and nonblended films", Biomaterials, vol. 24, pp. 537-547 (2003).

Urayama et al., "Controlled crystal nucleation in the melt-crystallization of poly(L-lactide) and poly(L-lactide)/poly(D-lactide) stereocomplex", Polymer, vol. 44, pp. 5635-5641 (2003).

Van Vlack, "Elements of Materials Science and Engineering", $6^{th}$ ed., 4 pages (1989).

Yash Khanna, "Rheological Mechanism and Overview of Nucleated Crystallization Kinetics", macromolecules, vol. 26, pp. 3639-3643 (1993).

International Search Report for PCT/US2009/053029, mailed Aug. 12, 2010, 5 pgs.

Borokhovskii et al., "Thermodynamic analysis of nucleus formation in crystallization of polymers", Vysokomol. Soyed. A18, No. 11, pp. 2406-2411 (1976).

Brostow, Performance of Plastics, Hanser Gardner Publicatons, $1^{st}$ Ed., pp. 254-255 (2000).

International Search Report for PCT/US2009/053182, mailed Nov. 9, 2009, 7 pgs.

* cited by examiner

IMPROVING FRACTURE TOUGHNESS OF MEDICAL DEVICES WITH A STEREOCOMPLEX NUCLEATING AGENT

BACKGROUND OF THE INVENTION

1. Field of the Invention

This invention relates to methods of manufacturing polymeric medical devices, in particular, stents.

2. Description of the State of the Art

This invention relates to radially expandable endoprostheses, that are adapted to be implanted in a bodily lumen. An "endoprosthesis" corresponds to an artificial device that is placed inside the body. A "lumen" refers to a cavity of a tubular organ such as a blood vessel. A stent is an example of such an endoprosthesis. Stents are generally cylindrically shaped devices that function to hold open and sometimes expand a segment of a blood vessel or other anatomical lumen such as urinary tracts and bile ducts. Stents are often used in the treatment of atherosclerotic stenosis in blood vessels. "Stenosis" refers to a narrowing or constriction of a bodily passage or orifice. In such treatments, stents reinforce body vessels and prevent restenosis following angioplasty in the vascular system. "Restenosis" refers to the reoccurrence of stenosis in a blood vessel or heart valve after it has been treated (as by balloon angioplasty, stenting, or valvuloplasty) with apparent success.

Stents are typically composed of scaffolding that includes a pattern or network of interconnecting structural elements or struts, formed from wires, tubes, or sheets of material rolled into a cylindrical shape. This scaffolding gets its name because it physically holds open and, if desired, expands the wall of the passageway. Typically, stents are capable of being compressed or crimped onto a catheter so that they can be delivered to and deployed at a treatment site.

Delivery includes inserting the stent through small lumens using a catheter and transporting it to the treatment site. Deployment includes expanding the stent to a larger diameter once it is at the desired location. Mechanical intervention with stents has reduced the rate of restenosis as compared to balloon angioplasty. Yet, restenosis remains a significant problem. When restenosis does occur in the stented segment, its treatment can be challenging, as clinical options are more limited than for those lesions that were treated solely with a balloon.

Stents are used not only for mechanical intervention but also as vehicles for providing biological therapy. Biological therapy uses medicated stents to locally administer a therapeutic substance. Effective concentrations at the treated site require systemic drug administration which often produces adverse or even toxic side effects. Local delivery is a preferred treatment method because it administers smaller total medication levels than systemic methods, but concentrates the drug at a specific site. Local delivery thus produces fewer side effects and achieves better results.

A medicated stent may be fabricated by coating the surface of either a metallic or polymeric scaffolding with a polymeric carrier that includes an active or bioactive agent or drug. Polymeric scaffolding may also serve as a carrier of an active agent or drug.

The stent must be able to satisfy a number of mechanical requirements. The stent must be capable of withstanding the structural loads, namely radial compressive forces, imposed on the stent as it supports the walls of a vessel. Therefore, a stent must possess adequate radial strength. Radial strength, which is the ability of a stent to resist radial compressive forces, is due to strength and rigidity around a circumferential direction of the stent. Radial strength and rigidity, therefore, may also be described as, hoop or circumferential strength and rigidity.

Once expanded, the stent must adequately maintain its size and shape throughout its service life despite the various forces that may come to bear on it, including the cyclic loading induced by the beating heart. For example, a radially directed force may tend to cause a stent to recoil inward. In addition, the stent must possess sufficient flexibility to allow for crimping, expansion, and cyclic loading.

Some treatments with implantable medical devices require the presence of the device only for a limited period of time. Once treatment is complete, which may include structural tissue support and/or drug delivery, it may be desirable for the stent to be removed or disappear from the treatment location. One way of having a device disappear may be by fabricating the device in whole or in part from materials that erode or disintegrate through exposure to conditions within the body. Thus, erodible portions of the device can disappear or substantially disappear from the implant region after the treatment regimen is completed. After the process of disintegration has been completed, no portion of the device, or an erodible portion of the device will remain. In some embodiments, very negligible traces or residue may be left behind. Stents fabricated from biodegradable, bioabsorbable, and/or bioerodable materials such as bioabsorbable polymers can be designed to completely erode only after the clinical need for them has ended.

However, there are potential shortcomings in the use of polymers, such as insufficient fracture toughness, as a material for implantable medical devices, such as stents.

SUMMARY OF THE INVENTION

Various embodiments of the present invention include a method of making a stent comprising: melt processing a polymer blend of PLLA and PDLA to allow formation of PLLA/PDLA stereocomplex crystallites in the blend during the processing; forming a tube from the melt processed blend comprising the stereocomplex crystallites, wherein the processed blend is quenched to a temperature below Tg of PLLA during formation of the tube; radially deforming the quenched polymer tube; and forming a stent from the deformed tube.

Further embodiments of the present invention include a method of making a stent comprising: melt processing a polymer blend of PLLA and PDLA to allow formation of PLLA/PDLA stereocomplex crystallites in the blend during the processing; forming a tube from the melt processed blend comprising the crystallites, wherein the processed blend is quenched to a temperature below Tg of PLLA during formation of the tube; annealing the quenched tube at a temperature above Tg of PLLA; and forming a stent from the annealed tube.

Additional embodiments of the present invention include a method of making a stent comprising: melt processing a polymer blend of PLLA and PDLA to allow formation of PLLA/PDLA stereocomplex crystallites in the blend during the processing; forming a tube from the melt processed blend comprising the crystallites; reducing a temperature of the tube below Tm of PLLA in a manner that allows growth of PLLA crystallites around the stereocomplex crystallites; deforming the polymer tube at a temperature below Tm of PLLA; and forming a stent from the deformed tube.

DETAILED DESCRIPTION OF THE INVENTION

Various embodiments of the present invention relate to manufacture of polymeric implantable medical devices. In particular, the embodiments include the use of a stereocomplex as a nucleating agent in forming a polymer construct to increase the fracture toughness of a device made from the construct. The methods described herein are generally applicable to polymeric implantable medical devices. In particular, the methods can be applied to tubular implantable medical devices such as self-expandable stents, balloon-expandable stents, stent-grafts, and pacemaker leads.

Figure 1:
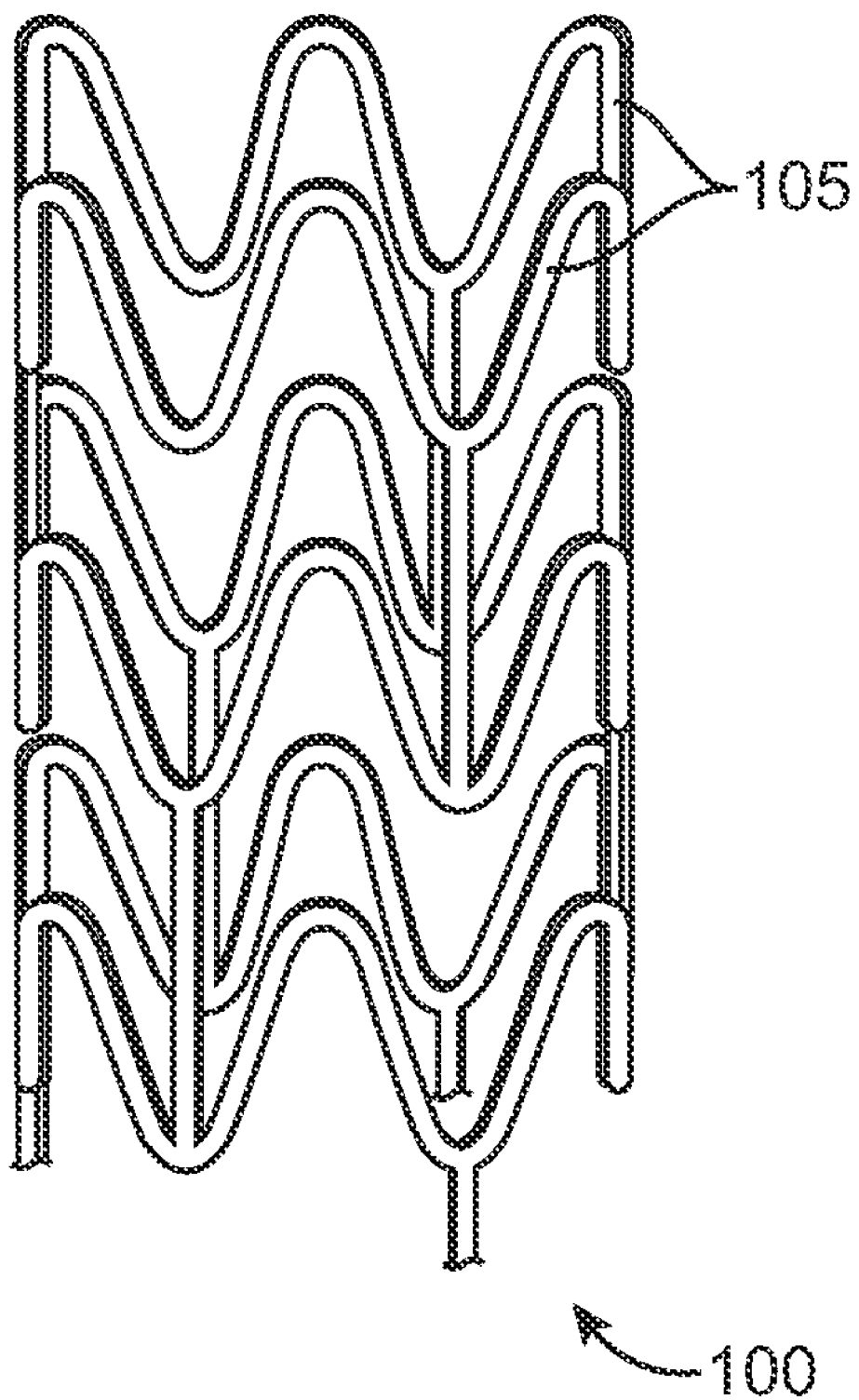
FIG. 1 depicts a stent.

A stent may include a pattern or network of interconnecting structural elements or struts. FIG. 1 depicts a view of a stent 100. In some embodiments, a stent may include a body, backbone, or scaffolding having a pattern or network of interconnecting structural elements 105. Stent 100 may be formed from a tube (not shown). The structural pattern of the device can be of virtually any design. The embodiments disclosed herein are not limited to stents or to the stent pattern illustrated in FIG. 1. The embodiments are easily applicable to other patterns and other devices. The variations in the structure of patterns are virtually unlimited. A stent such as stent 100 may be fabricated from a tube by forming a pattern with a technique such as laser cutting or chemical etching.

A stent such as stent 100 may be fabricated from a polymeric tube or a sheet by rolling and bonding the sheet to form the tube. A tube or sheet can be formed by extrusion or injection molding. A stent pattern, such as the one pictured in FIG. 1, can be formed in a tube or sheet with a technique such as laser cutting or chemical etching. The stent can then be crimped on to a balloon or catheter for delivery into a bodily lumen.

An implantable medical device can be made partially or completely from a biodegradable, bioabsorbable, or biostable polymer. A polymer for use in fabricating an implantable medical device can be biostable, bioabsorbable, biodegradable or bioerodable. Biostable refers to polymers that are not biodegradable. The terms biodegradable, bioabsorbable, and bioerodable are used interchangeably and refer to polymers that are capable of being completely degraded and/or eroded when exposed to bodily fluids such as blood and can be gradually resorbed, absorbed, and/or eliminated by the body. The processes of breaking down and absorption of the polymer can be caused by, for example, hydrolysis and metabolic processes.

A stent made from a biodegradable polymer is intended to remain in the body for a duration of time until its intended function of, for example, maintaining vascular patency and/or drug delivery is accomplished. After the process of degradation, erosion, absorption, and/or resorption has been completed, no portion of the biodegradable stent, or a biodegradable portion of the stent will remain. In some embodiments, very negligible traces or residue may be left behind.

The duration of a treatment period depends on the bodily disorder that is being treated. In treatments of coronary heart disease involving use of stents in diseased vessels, the duration can be in a range from about a month to a few years. However, the duration is typically up to about six months, twelve months, eighteen months, or two years. In some situations, the treatment period can extend beyond two years.

As indicated above, a stent has certain mechanical requirements such as high radial strength, high modulus, and high fracture toughness. A stent that meets such requirements greatly facilitates the delivery, deployment, and treatment of a diseased vessel. With respect to radial strength, a stent must have sufficient radial strength to withstand structural loads, namely radial compressive forces, imposed on the stent as it supports the walls of a vessel. In addition, the stent must possess sufficient flexibility to allow for crimping, expansion, and cyclic loading. A polymeric stent with inadequate radial strength can result in mechanical failure or recoil inward after implantation into a vessel.

The strength to weight ratio of polymers is smaller than that of metals. To compensate for the relatively low modulus, a polymeric stent can require significantly thicker struts than a metallic stent, which results in an undesirably large profile. One way of addressing the strength deficiency of polymers is to fabricate a stent from a deformed polymer construct. Deforming polymers tends to increase the strength along the direction of deformation. Thus, a stent fabrication process can include radially deforming a polymer tube and cutting a stent from the deformed tube.

With respect to toughness, a polymer stent should also have a high resistance to fracture. Semicrystalline polymers such as poly(L-lactide) (PLLA) that are suitable as stent materials tend to be brittle under biological conditions or conditions within a human body. Specifically, such polymers can have a glass transition temperature (Tg) above human body temperature which is approximately 37° C. These polymer systems exhibit a brittle fracture mechanism in which there is little or no plastic deformation prior to failure. As a result, a stent fabricated from such polymers can have insufficient toughness for the range of use of a stent. In particular, it is important for a stent to be resistant to fracture throughout the range of use of a stent, i.e., crimping, delivery, deployment, and during a desired treatment period.

A number of strategies may be employed to improve the fracture toughness of semicrystalline polymers such as PLLA. For example, a rubbery phase (or toughening agent) may be incorporated in the rigid polymer, such as polycaprolactone or polytrimethylcarbonate through chemical reaction or physical blending. However, this results in decreased strength and modulus.

Alternatively, fracture toughness can be improved by reducing the size of the polymer crystals or crystallites and increasing the density of the nuclei from which the crystals grow. Semicrystalline polymers can contain both amorphous and crystalline domains at temperatures below the melting point. Amorphous regions are those in which polymer chains are in relatively disordered configurations. Crystalline domains or crystallites are those in which polymer chains are in ordered configurations with segments of polymer chains essentially parallel to one another.

Generally, in the crystallization of polymers, there are two separate events that occur. The first event is the formation of nuclei in the polymer matrix. The second event is growth of the crystallite around these nuclei. The overall rate of crystallization of the polymer is dependent, therefore, on the equilibrium concentration of nuclei in the polymer matrix, and on the rate of growth of crystallites around these nuclei.

Figure 2:
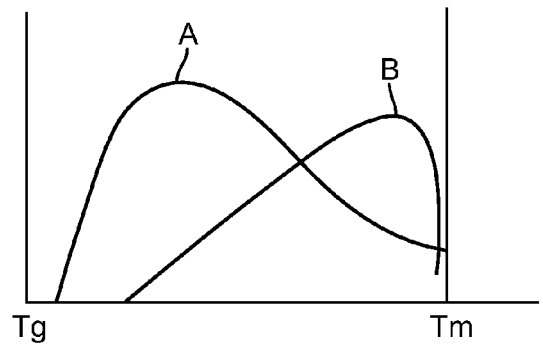
FIG. 2 depicts a schematic plot of the crystal nucleation rate and the crystal growth rate for a polymer.

In general, crystallization tends to occur in a polymer at temperatures between Tg and Tm of the polymer. FIG. 2 shows a schematic of the dependence of nucleation rate (A) and crystal growth rate (B) on temperature between the glass transition temperature (Tg) and the melting temperature (Tm) under quiescent conditions. At temperatures above Tg but far below Tm where polymer chain mobility is limited, nucleation is substantially favored over growth, since the latter process requires much more extensive chain mobility. These nuclei remain present in the polymer until its temperature is elevated above Tm for a period of time. A consequence of the behavior illustrated in FIG. 2 is that at high temperatures there are relatively few, large crystallites formed, while at low temperatures, there are relatively more numerous, smaller crystallites formed. Literature values (Medical Plastics and Biomaterials Magazine, March 1998) of ranges of Tg and Tm of PLLA are 173-178° C. and 60-65° C.

Nucleation density can be increased through the addition of nucleating agents, such as ethylenebis(12-hydroxystearylamide) (EBSA), cyclohexanedicarboxylic dianilide, tetramethylenedicarboxylic disalicyloylhydrazide, and hydrated magnesium silicate (talc). However, these small molecule materials do not have show good compatibility with polymers such as PLLA. Furthermore, the addition of these materials can cause deterioration of the mechanical properties of a polymer and potentially be a safety concern due to leaching out of these materials from the PLLA matrix.

Embodiments of the present invention involve processing a polymer with a stereocomplex to increase nucleation density and decrease crystal size to increase fracture toughness of a stent formed from the polymer. In particular, the embodiments include melt processing PLLA with a stereocomplex of PLLA and poly(D-lactic acid). Poly(lactic acid) (PLA) has three stereoisomers: poly(L-lactic acid) (PLLA), poly(D-lactic acid) (PDLA), and poly(DL-lactic acid) (PDLLA). PDLLA is an amorphous polymer. PLLA and PDLA are stereoisomers since they are mirror images of each other in terms of structure. Both of these stereoisomers are isotactic and semi-crystalline with a melting temperature (Tm) of about 180° C. and have identical mechanical properties. It has been shown in the scientific literature that upon blending, PLLA and PDLA co-crystallize to form stereocomplex crystals with a melting temperature of approximately 230° C., which is about 50° C. higher than the Tm of either PLLA or PDLA. The significant increase in melting temperature is believed to be due to the strong van der Waals interactions in the stereocomplex crystal structure.

The embodiments of the present invention apply generally to processing of a polymer construct that can be modified to form an implantable medical device. A polymer construct can be a polymer or polymer material formed into a geometrical shape, such as a tube or a sheet. The shape is chosen so that further processing can be applied to form an implantable medical device. For example, a stent pattern can be cut into a tube to form a stent. The polymer construct can be formed using extrusion or injection molding. Alternatively, a polymer tube may be formed from a sheet that is rolled and bonded into a tube.

Embodiments of the present invention include melt processing a polymer blend of PLLA and PDLA to allow formation of PLLA/PDLA stereocomplex crystallites in the blend during the processing. A tube is then formed from the processed blend which includes the stereocomplex crystallites that serve as nucleation sites for growth of PLLA crystallites. The concentration of PDLA is substantially less than PLLA to result in high nucleation density and low crystallite size, which provides for high fracture toughness.

Figure 3A:
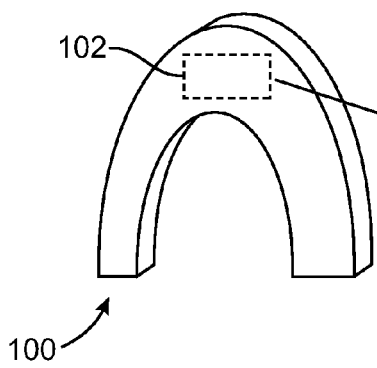
FIG. 3A depicts a strut of a polymeric stent fabricated without stereocomplex nucleating agent.
Figure 3B:
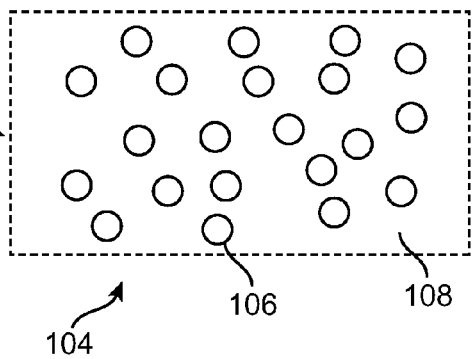
FIG. 3B is a schematic microstructure of a section of the strut of FIG. 3A.
Figure 4A:
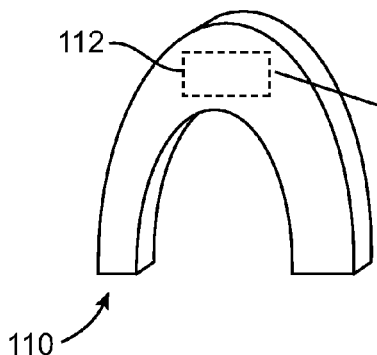
FIG. 4A depicts a strut of a polymeric stent fabricated with stereocomplex nucleating agent.
Figure 4B:
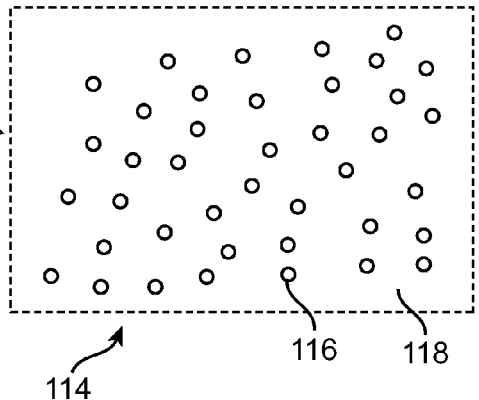
FIG. 4B is a schematic microstructure of a section of the strut of FIG. 4A.

FIG. 3A depicts a strut 100 of a polymeric stent fabricated without a stereocomplex nucleating agent and FIG. 3B is a schematic microstructure 104 of a section 102 of strut 100 showing a small amount of large crystals 106 dispersed within an amorphous region 108. FIG. 4A depicts strut 110 of a polymeric stent fabricated with a stereocomplex nucleating agent. FIG. 4B depicts the schematic microstructure 114 of a section 112 of strut 110 showing a large amount of smaller crystals 116 dispersed within an amorphous region 118.

The PLLA crystallite growth can be performed in more than one manner. In particular, two sets of embodiments are described herein. The melt processing of the polymer blend is the same for the two sets of embodiments. The sets of embodiments differ in processing of the blend after the melt processing.

In a first set of embodiments, the tube is initially formed from a polymer melt in a manner to reduce or prevent PLLA or PDLA crystallites. This is performed by quenching the tube following melt processing. The stereocomplex crystallites act as nucleation sites in a subsequent PLLA crystallite growth step. The crystal growth can be induced through deformation of the tube, annealing of the tube at crystallization temperature, or both. Additionally, the tube can optionally undergo a nucleation step to further increase nucleation density prior to the crystal growth in which the tube is annealed at a temperature or temperature range that allows PLLA nuclei formation with no or substantially no growth of crystallite around the PLLA nuclei or the stereocomplex crystallites.

In a second set of embodiments, the temperature of the tube is reduced from the melt processing temperature in manner that allows growth of PLLA crystallites around the stereocomplex crystallites.

In both the first and second set of embodiments, PLLA crystallites may be grown around the stereocomplex crystallites to obtain a desired degree of crystallinity. A stent can then be formed from the processed blend.

Additionally, in both the first and second set of embodiments, the temperature of the PLLA/PDLA blend during processing is above the Tm of PLLA and below Tm of the stereocomplex. Processing in this temperature range allows stereocomplex crystallites to be present in the melt with no crystallites of PLLA or PDLA. In some embodiments, the melt processing temperature is between 180-225° C.

As indicated above, the fracture toughness of the resultant tube and stent is enhanced by increasing nucleation density and therefore reducing the crystallite size. High nucleation density and small crystallite size can be provided by a blend in which the fraction of PDLA is substantially less than PLLA. The low fraction of PDLA allows formation of the small stereocomplex crystallites. In some embodiments, the weight fraction of PDLA in the PLLA/PDLA blend is less than 0.25 wt %, 0.25-5 wt %, 0.25-15 wt %, or 5-10 wt %. In other embodiments, the fraction of PDLA is even greater than 10 wt %.

The melt processing can be performed by batch processing or by continuous processing, such as extrusion. In general, extrusion refers to the process of conveying a polymer melt through a barrel of an extruder in which the melt is mixed, for example, through the use of rotating screws. The polymer melt can be forced through a die that imparts a selected shape to the polymer exiting the extruder. In the case of tubing extrusion, the polymer melt (extrudate) forced through the die forms a cylindrical film in the shape of a tube. The temperature of the film is reduced through cooling and can be drawn axially to form the final tube product.

An extruder generally includes a barrel through which a polymer melt is conveyed from an entrance to an exit port. The polymer can be fed to the extruder barrel as a melt or in a solid form below its melting temperature. The solid polymer is melted as it is conveyed through the barrel. The polymer in the extruder barrel is heated to temperatures above the melting temperature (Tm) of the polymer and exposed to pressures above ambient. The polymer within the barrel is mixed, for example, through the use of rotating screws. Representative examples of extruders for use with the present invention may include single screw extruders, intermeshing co-rotating and counter-rotating twin-screw extruders and other multiple screw masticating extruders.

In the embodiments of the present invention, PLLA and PDLA can be blended in an extruder. The temperature of the polymer melt in the barrel can be maintained in a temperature range between Tm of PLLA and Tm of the stereocomplex so that stereocomplex crystallites form within a PLLA melt. The blend including the stereocomplex crystallites is then be forced through a die to form a tube that includes stereocomplex crystallites dispersed within a PLLA matrix.

In other embodiments of the invention, a tube formed from the melt processed blend can be formed using injection molding. In general, "injection molding" refers to a manufacturing technique for making parts from polymers or plastic material. Molten plastic is injected at high pressure into a mold, which is the inverse of the desired shape. The mold can be made from metal, usually either steel or aluminum, and precision-machined to form the features of the desired part. In the embodiments of the present invention, a melt processed PLLA/PDLA blend with stereocomplex crystallites can be injected into a tubular mold.

In the first set embodiments mentioned above, the tube is formed in a manner that reduces or prevents PLLA or PDLA crystallites. The stereocomplex crystallites act as nucleation sites in a subsequent PLLA crystallite growth step. The crystal growth can be induced through deformation of the tube, annealing of the tube at crystallization temperature, or both.

In such embodiments, the tubular film from the extruder die can be quenched or rapidly cooled from the melt processing temperature to a temperature below Tg of PLLA. The tubular film can be quenched, for example, through immersion of the film in a batch of cold fluid such as water at a temperature of less than 25° C. or less than 0° C. The resultant tube can be composed of stereocomplex crystallites dispersed within an amorphous PLLA matrix.

With injection molding, the blend in the mold can be quenched from the melt processing temperature to a temperature below Tg of PLLA to reduce or prevent crystallization of the PLLA. The temperature of the mold can be controlled, for example, by a recirculating water bath. In one embodiment, the mold can be immersed or surrounded by a chamber containing water at a temperature that cools the mold to a desired temperature. In an embodiment, the channels for cooling water can be circulated through channels within the mold. As above, the resultant tube can be composed of stereocomplex crystallites dispersed within an amorphous or substantially amorphous PLLA matrix.

In these first set of embodiments, after formation of the tube composed of stereocomplex crystallites in the amorphous or substantially amorphous PLLA matrix, the tube is processed to grow PLLA crystals around the stereocomplex crystallites. These crystallites serve as nucleation sites for crystallite growth. A desired crystallinity may be at least 10-20%, 20-30%, 30-55%, or greater than 55%. As indicated above and described in detail below, crystallite growth can be induced by an increase in temperature, deformation, or both.

In some embodiments, PLLA crystals can be grown around the stereocomplex crystallites from the melt processing by annealing the tube at a temperature that allows PLLA crystallite growth around the stereocomplex crystallites. The temperature range for crystal growth can be any temperature between Tg and Tm that allows PLLA crystallite growth around the stereocomplex crystallites. For example, the temperature range can be at least $Tg+Z\times(Tm-Tg)$, where Z is 0.2-0.4, 0.4-0.8, or 0.8-0.9. PLLA crystallites can be allowed to grow for a selected crystallite growth time at the selected temperature. The crystal growth time depends on the crystallization rate (which depends on temperature as shown by FIG. 2) and the desired crystallinity. Thus, the faster the crystal growth rate, the shorter crystal growth time to achieve a desired crystallinity. PLLA nuclei can also form during this time period and crystallites can grow around such nuclei. The annealing time can be up to 5 min, 10 min, 30 min, or greater than 30 min.

Heating and maintaining a temperature of a tube at an annealing temperature or a crystallite growth temperature can be performed by various methods. For example, the tube can be heated in a vacuum oven. Alternatively, a warm gas such as nitrogen, oxygen, air, argon, or other gas can be blown on the tube. The temperature of the tube can be maintained by known control methods.

Figure 5:
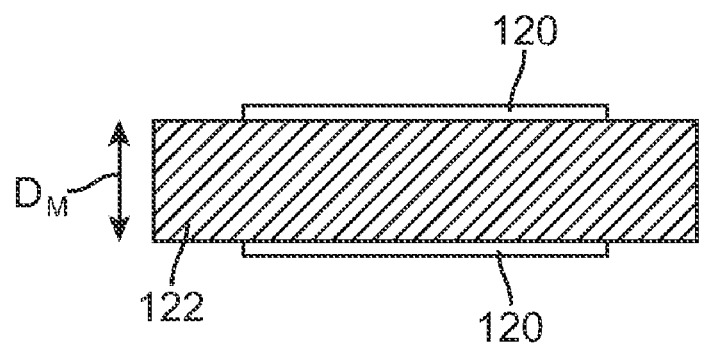
FIG. 5 depicts an axial cross-section of a polymer tube disposed over a mandrel with an inner diameter of the tube the same or substantially the same as an outer diameter of the mandrel.

A polymer construct may have a tendency to change shape upon heating. In particular a polymeric tube may tend to reduce in diameter or shrink upon heating. In some embodiments, the reduction in diameter of a polymer tube during the annealing step or temperature-induced crystal growth step can be reduced or prevented. Reduction in diameter can be reduced or prevented by disposing a polymeric tube over a mandrel during the heating. The shrinkage of the tube is limited to the outside diameter of the tube. To prevent reduction in diameter, the inside diameter of the tube can be the same or substantially the same as the outside diameter of the mandrel. FIG. 5 illustrates this with an axial cross-section of a polymer tube 120 disposed over a mandrel 122. An inner diameter of tube 120 is the same or substantially the same as an outer diameter Dm of mandrel 122.

Figure 6A:
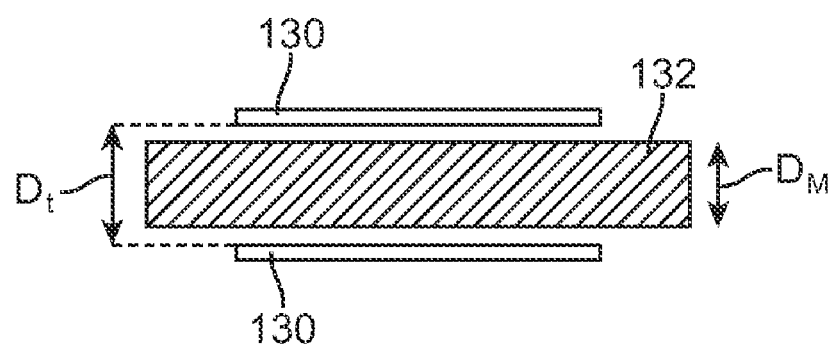
FIG. 6A depicts an axial cross-section of a polymer tube disposed over a mandrel with an inner diameter of the tube greater than an outer diameter of the mandrel.
Figure 6B:
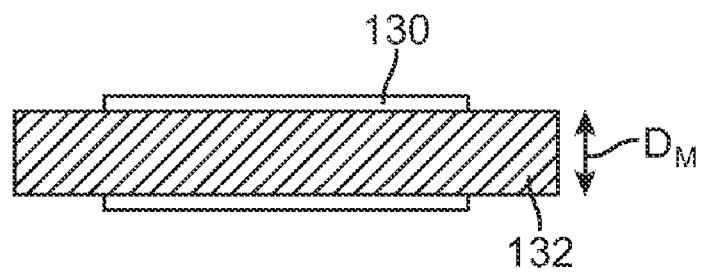
FIG. 6B shows the tube of FIG. 6A tube reduced in diameter due to heating.

To reduce shrinkage, the mandrel has an outside diameter less than the inside diameter of the polymer tube. FIG. 6A depicts this with an axial cross-section of a polymer tube 130 disposed over a mandrel 132. An inner diameter Dt of tube 130 is greater than an outer diameter Dm of mandrel 132. FIG. 6B shows that as tube 130 is heated during annealing or crystallite growth, tube 130 can reduce in diameter, but that the reduction in diameter is limited to the outer diameter Dm of the mandrel.

In further embodiments, shrinkage can be reduced or prevented by maintaining an increased pressure within the tube. For example, the polymer tube can be disposed in a mold, e.g., glass, and the internal pressure is increased during heating by blowing a gas in the tube.

After the crystallite growth step, the tube can then be subjected to further processing steps in the device fabrication process. For example, a stent pattern can be cut into the tube. Alternatively or additionally, the polymer tube can be deformed to increase the strength (as described below) prior to cutting a stent pattern.

In some embodiments, the PLLA crystallite growth can be induced directly through deformation of the tube. It can be desirable to include a radial deformation step of a tube in the manufacturing process of a stent to increase the strength along the direction of deformation as well as toughness. In particular, the tube can be radially deformed to increase its radial strength followed by formation of stent from the deformed tube. Additionally, the tube can be axially deformed to increase strength in the axial direction.

The radial and/or axial deformation induces crystal growth of PLLA crystallites around the stereocomplex crystallites from melt processing. Thus, in some embodiments, the polymer tube can be deformed after melt processing and quenching of the tube. In such embodiments, the deformation causes crystal growth around the stereocomplex crystallites. The tube can be radially deformed using known methods such as blow molding, that is described below.

In some embodiment, the temperature of the polymer tube during deformation can be lower or the same as the temperature during the annealing step. The deformation process can induce growth of crystallites around the stereocomplex crystallites formed during the melt processing. Growth of crystallites during deformation can occur even at temperatures at which there is little or no crystallite growth at quiescent conditions. As stated above, the schematic curve (B) for the crystal growth rate in FIG. 2 corresponds to quiescent conditions, and, thus, does not apply to the crystallite growth during deformation. The temperature of the polymer tube is desirably above Tg during deformation since as described below, Tg represents a transition from a vitreous state to a solid deformable or ductile state. Therefore, a temperature above Tg facilitates deformation of the polymer.

In$_{[y1]}$ other embodiments, the temperature of the tube during deformation can be even lower than the annealing temperature range. In such embodiments, growth of crystallites can be due to both the deformation and the increase in temperature. Exemplary temperature ranges of the tube during deformation can be $Tg+Y\times(Tm-Tg)$, where Y can be 0-0.2, 0.2-0.4, 0.4-0.8.

In still further embodiments, a temperature induced PLLA crystallite growth step and a deformation step can be performed sequentially. For example, the temperature can be increased to grow PLLA crystallites, followed by a deformation step at a selected temperature. Alternatively, a deformation step can be performed, followed by equilibrating the deformed construct at an increased temperature that allows PLLA crystallites to grow.

Figure 7A:
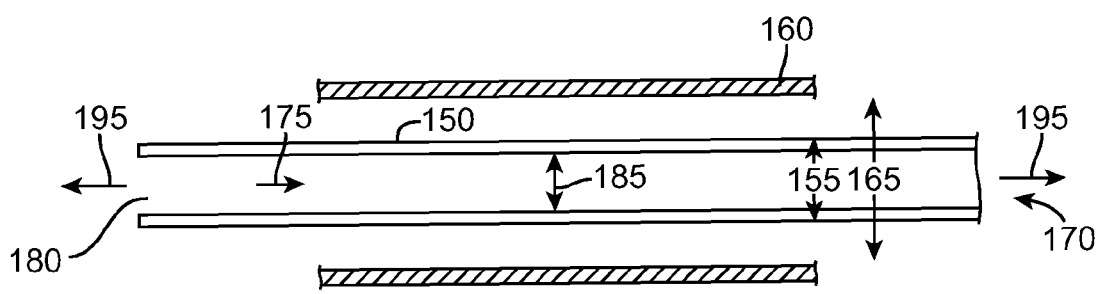
FIG. 7A depicts an axial cross-section of a polymeric tube positioned within a mold.
Figure 7B:
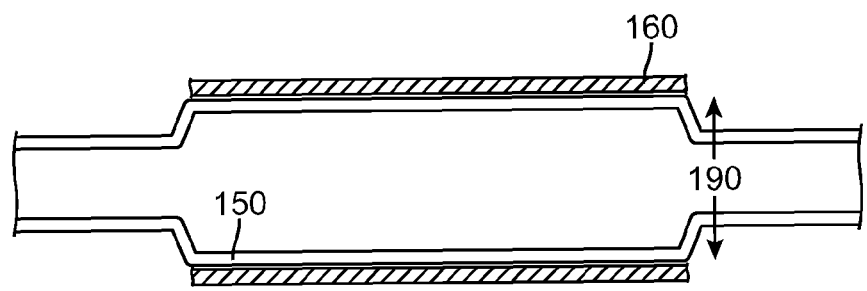
FIG. 7B depicts the polymeric tube of FIG. 7A in a radially deformed state.

FIGS. 7A-B illustrate an embodiment of deforming a polymeric tube using blow molding. FIG. 7A depicts an axial cross-section of a polymeric tube 150 with an outside diameter 155 positioned within a mold 160. Mold 160 limits the radial deformation of polymeric tube 150 to a diameter 165, the inside diameter of mold 160. Polymer tube 150 may be closed at a distal end 170 which may be open in subsequent manufacturing steps. A fluid is conveyed, as indicated by an arrow 175, into an open proximal end 180 of polymeric tube 150. A tensile force 195 can be applied at proximal end 180 and a distal end 170.

Polymeric tube 150 may be heated by heating the fluid to a temperature above ambient temperature prior to conveying the fluid into polymeric tube 150. Alternatively, the polymeric tube may be heated by heating the exterior of mold 160 by blowing a warm gas on the mold. The tube may also be heated by a heating element in the mold. The increase in pressure inside of polymer tube 150 facilitated by the increase in temperature of the polymeric tube causes radial deformation of polymer tube 150, as indicated by an arrow 185. FIG. 7B depicts polymeric tube 150 in a deformed state with an outside diameter 190 within mold 160.

Furthermore, the tube may be expanded to a target diameter. In one embodiment, the target diameter may be the diameter at which a stent pattern is formed by laser machining the tube. The target diameter can also correspond to the diameter of a stent prior to crimping. The degree of radial deformation may be quantified by a blow-up ratio or radial draw ratio:

$$\frac{\text{Outside Diameter of Deformed Tube}}{\text{Original Outside Diameter of Tube}}$$

In some embodiments, the radial draw ratio of a polymeric tube for use in fabricating a stent may be between about 1 and 10, or more narrowly between about 2 and 6. Similarly, the degree of axial deformation may be quantified by an axial draw ratio:

$$\frac{\text{Length of Deformed Tube}}{\text{Original Length of Tube}}$$

Additionally, in the first set of embodiments, the tube can optionally undergo a nucleation step prior to the crystal growth. In the nucleation step, the tube is annealed at a temperature or temperature range that allows PLLA nuclei formation with no or substantially no growth of crystallite around the PLLA nuclei or the stereocomplex crystallites. The annealing seeds PLLA nuclei throughout the polymer construct. The temperature range can be between Tg and 3, 5, 7, 10, 12, 15 or 18° C. above Tg. Alternatively, the temperature range can be Tg to $0.15\times(Tm-Tg)$. The annealing time can be up to 5 min, 10 min, 30 min, or greater than 30 min.

Figure 8:
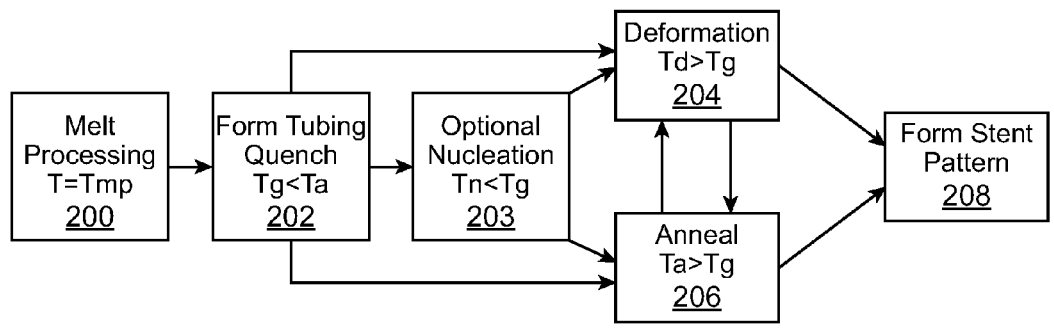
FIG. 8 depicts a flow chart of processing a PLLA/PDLA blend involving quenching a melt processed blend.
Figure 9:
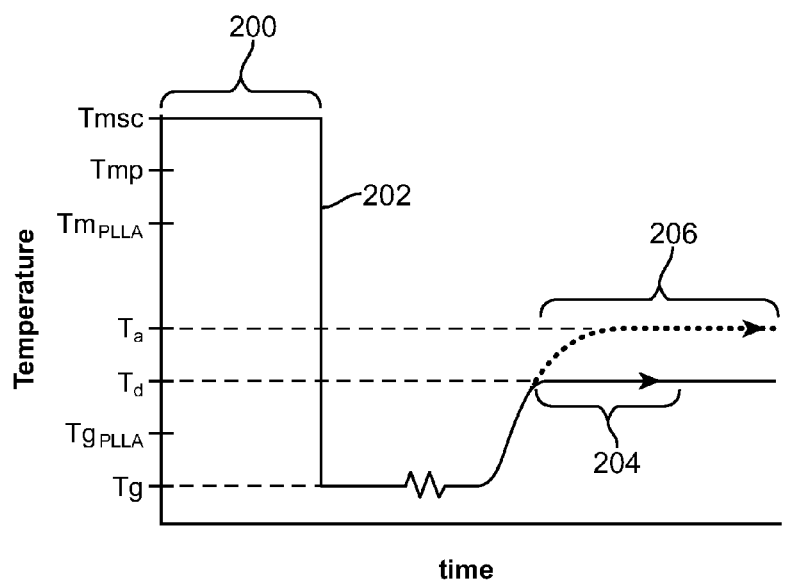
FIG. 9 depicts an exemplary temperature profile of the process depicted in FIG. 8.

FIG. 8 depicts a flow chart of the first set of embodiments of processing the PLLA/PDLA blend. FIG. 9 depicts an exemplary temperature profile. At step 200, the blend is melt processed at a melt processing temperature Tmp, which is between Tm of PLLA and Tm of the stereocomplex. A tube is formed from the blend at step 202 and quenched to a temperature Tq which is less than Tg of PLLA. The quench is illustrated by the steep drop in temperature shown in FIG. 9. The quenched tube can be deformed 204 at a temperature Td which is greater than Tg of PLLA. Alternatively, the quenched tube can be annealed 206 at a temperature Ta which is greater than Tg of PLLA. The quenched tube can optionally undergo a nucleation step 203 prior to deforming 204 or crystal growth annealing 206 in which the tube is annealed at a nucleation temperature Tn>Tg. FIG. 9 shows Ta>Td, however, Ta can be the same or less than Td. As shown in FIG. 8, a deformation step 204 can be followed by an annealing step

206 and an annealing step 206 can be followed by deformation 204. After deformation, annealing, or both, a stent pattern can be formed 208 on the tube.

As discussed above, in the second set of embodiments, the temperature of the tube is reduced from the melt processing temperature in manner that allows growth of PLLA crystallites around the stereocomplex crystallites. In such embodiments, the temperature of the tube is reduced from the melt processing temperature to a temperature below the Tm of PLLA. PLLA crystallites grow around the stereocomplex crystallites during the temperature reduction. The temperature can eventually be reduced to below Tg of PLLA, however, growth of PLLA crystallites is facilitated prior reaching Tg. This is in contrast to the first set of embodiments in which PLLA crystallite growth is reduced or prevented by quenching the tube from the melt processing temperature to below Tg.

In some embodiments, the tube can be annealed at a temperature between Tg and Tm of PLLA following the temperature reduction. In such embodiments, the temperature can be reduced to a temperature or temperature range between Tg and Tm of PLLA and maintained at this temperature or temperature range for a period of time. For example, the temperature can be at least $Tg+Z\times(Tm-Tg)$, where Z is 0.2-0.4, 0.4-0.8, or 0.8-0.9. PLLA crystallite can be allowed to grow for a selected crystallite growth time at the selected temperature. PLLA nuclei can also form and crystallites can grow around such nuclei. The annealing time can be up to 5 min, 10 min, 30 min, or greater than 30 min.

Additionally, the polymer tube is deformed during the temperature reduction, the annealing, or both the temperature reduction and annealing. In such embodiments, the polymer tube can be deformed while in a temperature range between Tg and Tm of PLLA. In these embodiments, the tube can be deformed radially, axially, or both radially and axially. A stent can then be formed from the deformed tube.

As above, the tube can be formed using either extrusion or injection molding. In some embodiments, a tubular film forced through a die can be cooled with a fluid that provides a desired cooling rate of the tubular film from the melt processing temperature. The fluid can be a gas blown into or onto the tubular film. The tubular film can also be passed through a bath of liquid such as water. The temperature of the cooling fluid can be 10, 20, 30, or more than 30° C. above Tg of PLLA. Following the cooling period or annealing, the tube can then be quenched below the Tg of PLLA.

An extruded tube can be radially deformed using, for example, blown-film extrusion. The molten polymer is extruded through a die onto a mandrel and the tube expanded around an air bubble that is sealed at both ends. Alternatively, the extruded tube can be expanded using blow molding, as described above.

Figure 10:
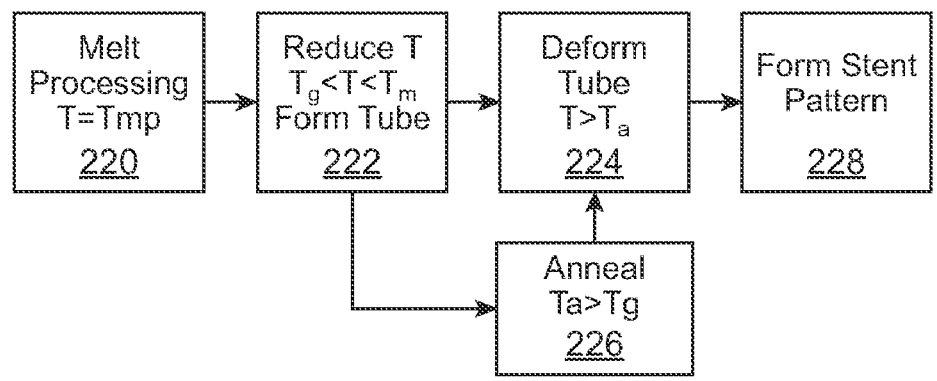
FIG. 10 depicts a flow chart of processing a PLLA/PDLA blend involving gradual cooling of a melt processed blend.
Figure 11:
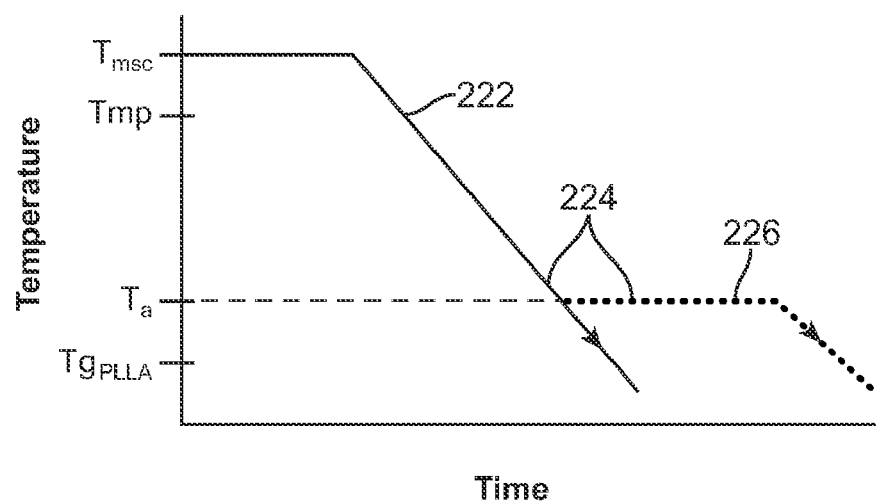
FIG. 11 depicts an exemplary temperature profile of the process depicted in FIG. 10.

FIG. 10 depicts a flow chart of the second set of embodiments of processing the PLLA/PDLA blend. FIG. 11 depicts an exemplary temperature profile. As in the first set of embodiments, the blend is melt processed 220 at a melt processing temperature Tmp, which is between Tm of PLLA and Tm of the stereocomplex. At step 222, a tube is formed from the blend and the temperature is reduced to below Tm of PLLA. The reduction in temperature is illustrated by the gradual drop in temperature shown in FIG. 11. As shown by the temperature profile in FIG. 11, the temperature can be reduced to below Tg. The tube can optionally be annealed 226 at a temperature Ta which is above Tg of PLLA. The tube is radially and/or axially deformed 224 during the reduction in temperature, annealing, or both. After the deformation, a stent pattern can be formed 228 on the tube.

For the purposes of the present invention, the following terms and definitions apply:

The "glass transition temperature," Tg, is the temperature at which the amorphous domains of a polymer change from a brittle vitreous state to a solid deformable or ductile state at atmospheric pressure. In other words, the Tg corresponds to the temperature where the onset of segmental motion in the chains of the polymer occurs. When an amorphous or semi-crystalline polymer is exposed to an increasing temperature, the coefficient of expansion and the heat capacity of the polymer both increase as the temperature is raised, indicating increased molecular motion. As the temperature is raised the actual molecular volume in the sample remains constant, and so a higher coefficient of expansion points to an increase in free volume associated with the system and therefore increased freedom for the molecules to move. The increasing heat capacity corresponds to an increase in heat dissipation through movement. Tg of a given polymer can be dependent on the heating rate and can be influenced by the thermal history of the polymer. Furthermore, the chemical structure of the polymer heavily influences the glass transition by affecting mobility. As used herein, unless otherwise specified, "Tg", refers to the Tg of PLLA.

"Strength" refers to the maximum stress along an axis which a material will withstand prior to fracture. The ultimate strength is calculated from the maximum load applied during the test divided by the original cross-sectional area.

"Modulus" may be defined as the ratio of a component of stress or force per unit area applied to a material divided by the strain along an axis of applied force that results from the applied force. For example, a material has both a tensile and a compressive modulus.

"Strain" refers to the amount of expansion or compression that occurs in a material at a given stress or load. Strain may be expressed as a fraction or percentage of the original length, i.e., the change in length divided by the original length. Strain, therefore, is positive for expansion and negative for compression.

The tensile stress on a material may be increased until it reaches a "tensile strength" which refers to the maximum tensile stress which a material will withstand prior to fracture. The ultimate tensile strength is calculated from the maximum load applied during a test divided by the original cross-sectional area. Similarly, "compressive strength" is the capacity of a material to withstand axially directed pushing forces. When the limit of compressive strength is reached, a material is crushed.

"Stress" refers to force per unit area, as in the force acting through a small area within a plane. Stress can be divided into components, normal and parallel to the plane, called normal stress and shear stress, respectively. Tensile stress, for example, is a normal component of stress applied that leads to expansion (increase in length). In addition, compressive stress is a normal component of stress applied to materials resulting in their compaction (decrease in length). Stress may result in deformation of a material, which refers to a change in length. "Expansion" or "compression" may be defined as the increase or decrease in length of a sample of material when the sample is subjected to stress.

"Toughness" is the amount of energy absorbed prior to fracture, or equivalently, the amount of work required to fracture a material. One measure of toughness is the area under a stress-strain curve from zero strain to the strain at fracture. The units of toughness in this case are in energy per unit volume of material. See, e.g., L. H. Van Vlack, "Elements of Materials Science and Engineering," pp. 270-271, Addison-Wesley (Reading, Pa., 1989).

EXAMPLE

The example set forth below are for illustrative purposes only and are in no way meant to limit the invention. The following example is given to aid in understanding the invention, but it is to be understood that the invention is not limited to the particular example. The Example below is provided by way of illustration only and not by way of limitation. The parameters and data are not to be construed to limit the scope of the embodiments of the invention.

Example 1

Preparation of PLLA Stent from Extruded and Expanded Tubing Using PLLA/PDLA Stereocomplex as Nucleating Agent Step 1 (material mixing): 20 g PDLA (Mw≈600 kg/mol) is mixed with 1 kg of high molecular weight PLLA (Mw≈600 kg/mol) through melt compounding using a twin screw extruder at 200° C., or through solution blending by dissolving both PLLA and PDLA in chloroform and precipitating them into methanol.

Step 2 (tubing extrusion): The mixed PDLA/PLLA material is extruded in a single screw extruder at 200° C. and directly quenched in cold water. The size of the extruded tubing is set at about 0.02" for inside diameter (ID) and 0.06" for outside diameter (OD).

Step 3 (tubing expansion): The extruded tubing is placed in a glass mold and expanded at about 200° F. to increase its crystallinity and biaxial orientation. The final ID and OD of the expanded tubing are set at 0.10" and 0.11", respectively.

Step 4 (stent preparation): A stent is cut from the expanded tubing using a femto-second laser, crimped to a smaller size (0.05") on a balloon catheter and sterilized by an electron beam at a dose of 25 kGray.

Example 2

Preparation of PLLA Stent from Extruded Tubing Using PLLA/PDLA Stereocomplex as Nucleating Agent Step 1 (material blending): 60 g PDLA (Mw≈600 kg/mol) is blended with 1 kg of high molecular weight PLLA (Mw≈600 kg/mol) through melt compounding in a twin screw extruder at 200° C.

Step 2 (tubing extrusion): The PDLA/PLLA blend is extruded in a single or twin screw extruder at 200° C. and slowly cooled down in warm/hot water before it's finally quenched in cold water. The size of the extruded tubing is set at about 0.07" for ID and 0.08" for OD.

Step 3 (stent preparation): A stent is directly cut from the extruded tubing using a femto-second laser, crimped down to a smaller size (0.05") on a balloon catheter and sterilized by an electron beam at a dose of 25 kGray.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A method of making a stent comprising:
    melt processing a polymer blend of PLLA and PDLA to allow formation of PLLA/PDLA stereocomplex crystallites in the blend during the processing, wherein he blend comprises 0.25 to 15 wt % PDLA;
    forming a tube from the melt processed blend comprising the stereocomplex crystallites, wherein the processed blend is quenched to a temperature below Tg of PLLA during formation of the tube;
    annealing the quenched tube at a temperature that allows formation of PLLA nuclei with no or substantially no growth of crystallites around the PLLA nuclei or the stereocomplex crystallites prior to the radial deformation of the tube;
    radially deforming the annealed polymer tube; and
    forming a stent from the deformed tube.

2. The method of claim 1, wherein the temperature range of annealing is Tg(PLLA)+Z(Tm(PLLA)−Tg(PLLA)) wherein Z is selected from the group consisting of 0.2-0.4, 0.4-0.8 and 0.8-0.9.

3. The method of claim 1, wherein the radial deformation induces growth of PLLA crystallites around the stereocomplex crystallites.

4. The method of claim 1, wherein the melt processing comprises extrusion or injection molding.

5. The method of claim 1, wherein the stereocomplex crystallites are dispersed throughout the formed tube.

6. The method of claim 1, wherein the melt processing temperature is 180-225° C.

7. The method of claim 1, wherein the temperature of the blend during melt processing is between Tm of PLLA and Tm of the stereocomplex.

8. The method of claim 1, wherein the quenching reduces or prevents PLLA crystallization during formation of the tube.

9. The method of claim 1, wherein the stereocomplex increases the nucleation density of the polymer tube.

10. The method of claim 1, wherein the crystallinity of the radially deformed tube is 25 to 55%.

11. A method of making a stent comprising:
    melt processing a polymer blend of PLLA and PDLA to allow formation of PLLA/PDLA stereocomplex crystallites in the blend during the processing, wherein the blend comprises 0.25 to 15 wt % PDLA;
    forming a tube from the melt processed blend comprising the crystallites, wherein the processed blend is quenched to a temperature below Tg of PLLA during formation of the tube;
    annealing the quenched tube at a temperature that allows formation of PLLA nuclei with no or substantially no growth of crystallites around the PLLA nuclei or the stereocomplex crystallites followed by annealing at a temperature above Tg of PLLA that allows growth of PLLA crystallites around the PLLA nuclei and the stereocomplex crystallites; and
    forming a stent from the annealed tube.

12. The method of claim 11, further comprising radially deforming the annealed tube.

13. The method of claim 11, wherein the melt processing comprises extrusion or injection molding.

14. The method of claim 11, wherein the stereocomplex crystallites are dispersed throughout the formed tube.

15. The method of claim 11, wherein the melt processing temperature is 180-225° C.

16. The method of claim 11, wherein the temperature of the blend during melt processing is between Tm of PLLA and Tm of the stereocomplex.

17. The method of claim 11, wherein the quenching reduces or prevents PLLA crystallization during formation of the tube.

18. The method of claim 11, wherein the stereocomplex crystallites increase the nucleation density of the polymer tube.

19. The method of claim 11, wherein the annealing further increases the nucleation density of the polymer tube.

20. The method of claim 11, wherein the crystallinity of the annealed tube is 25 to 55% after annealing.

21. A method of making a stent comprising:
melt processing a polymer blend of PLLA and PDLA to allow formation of PLLA/PDLA stereocomplex crystallites in the blend during the processing, wherein the blend comprises 0.25 to 15 wt % PDLA;
forming a tube from the melt processed blend comprising the crystallites;
reducing a temperature of the tube below Tm of PLLA in a manner that allows growth of PLLA crystallites around the stereocomplex crystallites;
deforming the polymer tube at a temperature below Tm of PLLA; and
forming a stent from the deformed tube.

22. The method of claim 21, wherein the temperature of the tube is reduced from the melt processing temperature to a temperature above Tg of PLLA and quenched to below Tg of PLLA.

23. The method of claim 21, wherein the polymer tube is deformed radially, axially, or both at a temperature above Tg of PLLA.

* * * * *